United States Patent [19]

Hussain et al.

[11] 4,241,055

[45] Dec. 23, 1980

[54] DERIVATIVES OF ASPIRIN

[75] Inventors: Anwar A. Hussain, Lexington, Ky.; James E. Truelove, Douningtown, Pa.; Harry B. Kostenbauder, Lexington, Ky.

[73] Assignee: The University of Kentucky Research Foundation, Lexington, Ky.

[21] Appl. No.: 43,815

[22] Filed: May 30, 1979

[51] Int. Cl.³ .................. A61K 31/70; C07H 13/02
[52] U.S. Cl. .......................... 424/180; 424/230; 424/235; 536/115; 536/119; 536/18
[58] Field of Search .............. 424/180, 230, 235; 536/115, 119

[56] References Cited

U.S. PATENT DOCUMENTS

| | | | |
|---|---|---|---|
| 3,118,875 | 1/1964 | Adams, Jr. ................ | 536/18 |
| 3,279,990 | 10/1966 | Rose et al. ................ | 536/119 |
| 3,639,169 | 2/1972 | Broeg et al. ............... | 424/230 |
| 3,764,668 | 10/1973 | Higuchi et al. ............. | 424/230 |
| 3,887,700 | 6/1975 | Boncey et al. ............. | 424/230 |
| 4,126,681 | 11/1978 | Reller ...................... | 424/235 |

OTHER PUBLICATIONS

Turner, "Chem. Abst." vol. 58, 1963, pp. 11459–11460.

*Primary Examiner*—Johnnie R. Brown
*Attorney, Agent, or Firm*—Burns, Doane, Swecker & Mathis

[57] ABSTRACT

There are provided novel derivatives of 2-acetoxybenzoic acid, which are substituted 1-0-(2'acetoxy)benzoyl-α-D-2-deoxyglucopyranose derivatives and are suitable for the attainment of high 2-acetoxybenzoic acid blood levels without irritation of the gastrointestinal lining.

22 Claims, No Drawings

DERIVATIVES OF ASPIRIN

CROSS-REFERENCE TO RELATED APPLICATION

Hussain et al copending application, Ser. No. 043,814, filed concurrently herewith, and hereby expressly incorporated by reference.

BACKGROUND OF THE INVENTION

1. Field of the Invention

The present invention relates to 2-acetoxybenzoic acid and more particularly, the present invention relates to therapeutically useful derivatives of 2-acetoxybenzoic acid, which are substituted 1-O-(2'-acetoxy)benzoyl-α-D-2-deoxyglucopyranose derivatives.

The novel compounds of this invention exhibit analgesic, antipyretic, and antirheumatic therapeutic activity.

The compound 2-acetoxybenzoic acid is commonly known as "aspirin" and/or "acetylsalicylic acid", and is one of the most widely used compounds in the treatment of simple pain and inflammation. 2-Acetoxybenzoic acid is widely employed as an analgesic, an antipyretic, and anti-inflammatory and an antirheumatic agent, and it is particularly useful in the relief of fever, headache, myalgia, arthralgia and other pains associated with integumental structures. 2-Acetoxybenzoic acid is generally administered for these conditions in the form of powder, particle, capsule, solution, tablet or other pharmaceutically acceptable dosage form because it is advantageous from the standpoint that chronic use of the compound will not lead to a tolerance or addiction thereof. Moreover, its toxicity is much lower than most compounds possessing similar pharmacologic activity. However, 2-acetoxybenzoic acid, as used for these purposes, is well-known by the practicing skilled artisan of the medical arts to exhibit certain unwanted and deliterious side effects. Specifically, it induces occult hemorrhaging in the gastrointestinal tract, which results from contact of the insoluble solid particulate of the compound with the gastrointestinal mucosa. As a result of this insolubilization, the very acidic particles of 2-acetoxybenzoic acid will adhere to the gastrointestinal mucosa in the form of crystals and such crystals, taken together with the acidic environment of the gastrointestinal lining, will produce microetching thereof, which in turn, leads to gastrointestinal bleeding.

2. Description of the Prior Art

To date, it is known that gastric bleeding can be diminished if (1) an aqueous solution of 2-acetoxybenzoic acid is administered, or (2) a buffered aqueous solution of 2-acetoxybenzoic acid is administered. However, such solutions leave much to be desired in that they are commercially and consumerwise unacceptable, i.e., water and/or buffered solutions are unacceptable as a suitable pharmaceutical dosage form.

One product on the market, commercially known as "Alka-Seltzer ®" is basically an alkaline effervescent 2-acetoxybenzoic acid formulation, which does exhibit satisfactory water solubility and dissolution, insofar as 2-acetoxybenzoic acid is concerned. However, at least three disadvantages are associated with this product. Firstly, the product is contained in a tablet form and must initially be dissolved in water prior to consumption. Secondly, because the product contains a high amount of sodium ion, it is unacceptable for administration to hypertensive patients (those who suffer from high blood pressure), because it has now been medically established that the sodium ion contributes to hypertension. Thirdly, the alkaline nature of the product per se alters the pH of the blood and urine to the alkaline side. Chronic use of this product could thus initiate alkalosis.

It has also been proposed to avoid the adverse effects of 2-acetoxybenzoic acid by the use of various esterified derivatives thereof, wherein transient blocking of the acidic carboxylic group of aspirin occurs. For instance, French Patent No. M1453 describes various antipyretic and analgesic compounds formed by esterifying 2-acetoxybenzoic acid with various sugars. Whether such derivates are viable substitutes for 2-acetoxybenzoic acid depends not only upon whether these derivatives have therapeutic value per se, but to a larger extent upon whether these derivatives have the potential to revert to 2-acetoxybenzoic acid by hydrolysis in vivo.

In this respect, it is notable that certain derivatives of 2-acetoxybenzoic acid tend to hydrolyze so as to form the corresponding ester of salicylic acid and not aspirin. The following reaction scheme serves to illustrate the manner in which derivatives of 2-acetoxybenzoic acid may hydrolyze:

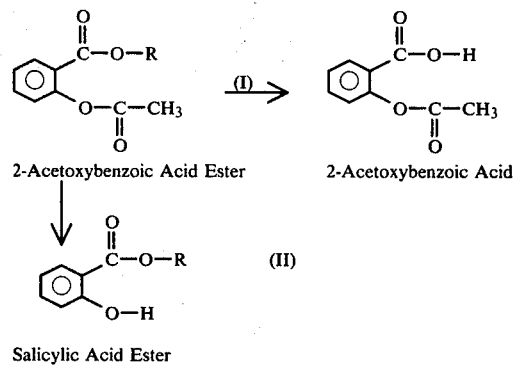

It is apparent that only those esterified derivatives of 2-acetoxybenzoic acid which hydrolyze according to reaction scheme (I), so as to produce aspirin, are viable substitutes for aspirin. Also, such a substitute must hydrolyze at a rate sufficient to release aspirin in therapeutically effective quantities.

It has recently been discovered that the aspirin derivative, 1-O-(2'-acetoxy)benzoyl-α-D-glucopyranose, tends to hydrolyze so as to form the corresponding sugar derivative of salicylic acid, as per reaction scheme (II) depicted above. Furthermore, to the extent that hydrolysis to aspirin takes place, such hydrolysis takes place only at a very slow rate. Cf. the aforenoted Hussain et al application, Ser. No. 043,814.

In summary, the various prior art sugar derivatives of 2-acetoxybenzoic acid present a non-irritating neutral molecule to the gastrointestinal lining when administered for therapeutic purposes. However, the group which blocks the carboxylic acid function of 2-acetoxybenzoic acid tends to be bound thereto very tightly. Such prior art derivatives, therefore, do not release aspirin in vivo in therapeutically sufficient quantities. Thus, a need exists for a 2-acetoxybenzoic acid derivative, wherein transient blocking of the carboxylic function occurs, yet wherein the blocking group is not so tenaciously bound thereto.

SUMMARY OF THE INVENTION

Accordingly, it is one object of the present invention to provide a derivative of 2-acetoxybenzoic acid which does not tend to cause local irritation of the gastrointestinal tract, yet which is capable of hydrolyzing at a rate sufficient to release 2-acetoxybenzoic acid in vivo in therapeutically sufficient quantities.

It is another object of the present invention to provide a derivative of 2-acetoxybenzoic acid which will permit a therapeutically effective compound to be absorbed through the gastrointestinal lining, in a manner such that insoluble, acidic particles of 2-acetoxybenzoic acid are not contacted therewith, thus eliminating gastrointestinal bleeding.

Finally, it is yet another object of the present invention, to provide a derivative of 2-acetoxybenzoic acid, which can be formulated in a suitable oral pharmaceutically acceptable dosage form for administration as an analgesic, an antipyretic, an anti-inflammatory and an antirheumatic agent to warm-blooded animals.

These and other objects of the instant invention will become more readily apparent from a reading of the accompanying disclosure and appended claims thereto.

The foregoing objects are attained with the use of novel acylal derivatives of 2-acetoxybenzoic acid, the structure of which may be represented by the following formula I

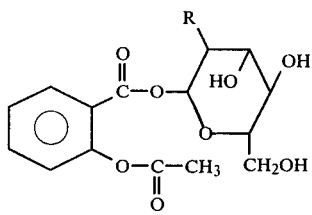

wherein R represents amino, lower monoalkylamino, lower dialkylamino, lower alkyl, lower cycloalkyl, lower hydroxy-substituted alkyl, lower alkoxy or piperidino.

DETAILED DESCRIPTION OF THE INVENTION

If the substituent R within the compounds of formula I includes lower alkyl groups, these alkyl group contain e.g., 1-4 carbon atoms. If the lower alkyl is unsubstituted, methyl is preferred; in the case of hydroxy-substituted alkyl, 2-hydroxy-alkyl is preferred. Lower cycloalkyl groups R may comprise e.g., 3-5 carbon atoms.

The compounds of formula I can be synthesized according to the following scheme:

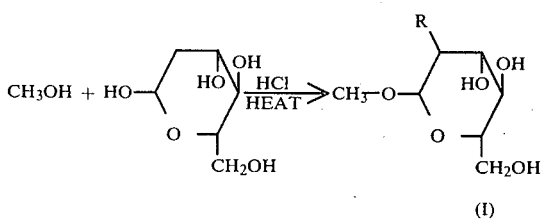

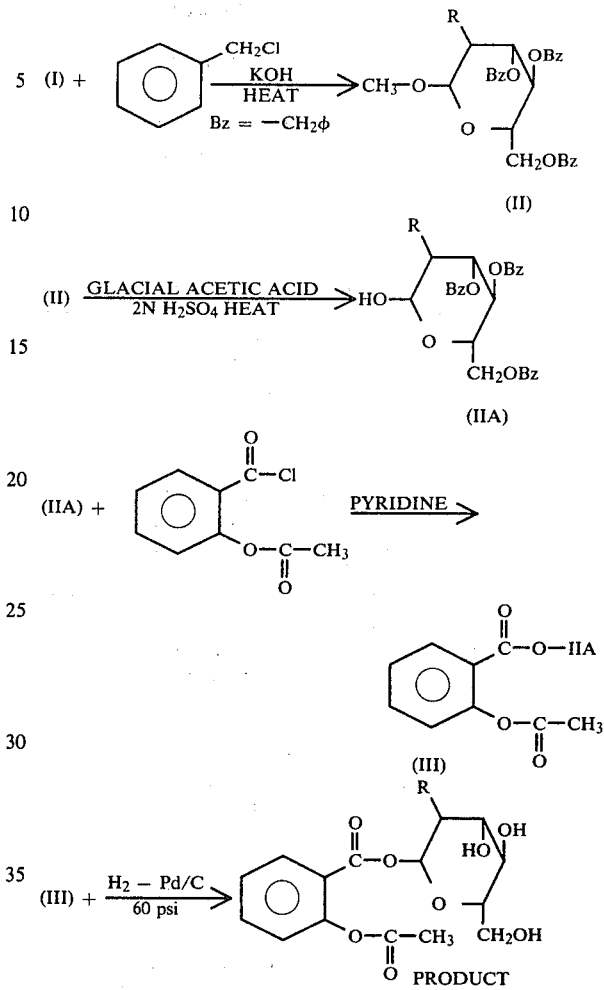

The above method is basically a modification of the method reported by Glaudemans and Fletcher in *Methods of Carbonhydrate Chemistry*, Volume VI, R. L. Whistler and J. N. Bemiller, Eds., Academic Press, New York, N.Y. (1972), pp. 373–376.

Numerous modifications in the depicted reaction scheme will be apparent to those skilled in the art. For example, protecting groups other than benzyl can be employed, so long as they can be readily removed after coupling of the substituted α-D-2-deoxyglucopyranose and the 2-acetoxybenzoic acid portions of the molecule. Thus, p-methoxybenzyl or tert-butyl radicals could be introduced into the glucopyranose derivative instead of the benzyl protecting groups. After coupling, benzyl and p-methoxybenzyl protecting groups can be conveniently removed by catalytic hydrogenolysis. Suitable catalysts may include rhodium, platinum, ruthenium, Raney nickel, and palladium (optionally on a support), a particularly preferred catalyst being palladium-on-carbon. When protecting groups which are normally not sensitive to catalytic hydrogenolysis, e.g., tert-butyl radicals, are employed, removal may be effected by use of an acid such as trifluoroacetic acid. If R is hydroxyalkyl group, the latter, of course, will react towards any protective group in the same manner as the hydroxymethyl group in 5-position of the glucopyranose nucleus.

Variations in the coupling reaction would also be possible. For example, the acid chloride starting material could be reacted with the protected glucopyranose in the presence of suitable bases other than pyridine, e.g., other tertiary aliphatic or aromatic amines such as N-methylmorpholine, triethylamine, and picoline, conveniently in a non-protic solvent. Alternatively, the protected glucopyranose could be reacted with 2-acetoxybenzoic acid (rather than with the acid chloride), in which case the reaction would be conducted in the presence of a suitable dehydrating agent, for example, an aromatic or aliphatic carbodiimide.

The rate of generation of aspirin via hydrolysis of its derivatives of the present invention can be determined spectrophotometrically. Determination of rate of generation of aspirin from its pro-drugs according to the present invention were made using solutions ranging from pH 1.2 to pH 9.

The generation of aspirin from the derivatives was found to be largely independent of the pH of the solutions. The half-life for the hydrolysis at pH 3 and pH 8 at 37° C. was found to be in the range of several minutes, e.g., between 5 and 10 minutes.

Thus, the transient blocking of the acidic carboxylic group of aspirin by formation of an acylal-linked derivative results in a compound which regenerates aspirin at an acceptable rate. Such a compound reduces the gastrointestinal liability of aspirin by presenting a neutral molecule to the gastric membrane.

The compounds of this invention are conveniently administered in oral dosage form, such as by tablet or capsule, by combining the same in a therapeutic amount (e.g., dosage regimen for aspirin on an equivalent weight basis) with any oral pharmaceutically acceptable inert carrier, such as lactose, starch (pharmaceutical grade), dicalcium phosphate, calcium sulfate, kaolin, mannitol, and powdered sugar. In addition, when required, suitable binders, lubricants, disintegrating agents, and coloring agents can also be added. Typical binders include starch, gelatin, sugars, such as sucrose, molasses, and lactose, natural and synthetic gums such as acacia, sodium alginate, extract of Irish moss, carboxymethylcellulose, methylcellulose, and polyvinylpyrrolidone, polyethyleneglycol, ethylcellulose and waxes. Typical lubricants for use in these dosage forms can include, without limitation, sodium benzoate, sodium acetate, sodium chloride, leucine and polyethyleneglycol. Suitable disintegrators can include, without limitation, starch, methylcellulose, agar, bentonite, cellulose and wood products, alginic acid, guar gum, citrus pulp, carbonmethylcellulose and sodium lauryl sulfate. If desired, a conveniently pharmaceutically acceptable dye can be incorporated into the dosage unit form, i.e., any of the standard FD&C dyes.

Any skilled artisan can prepare these oral dosage forms by simply referring to the oral dosage form preparatory procedure outlined in "REMINGTON'S PHARMACEUTICAL SCIENCES," Fourteenth Edition (1970), pp. 1659-1698, inclusive.

The dose administered, whether a single dose or a daily dose will, of course, vary with the needs of the individual being treated. However, the dosage administered is not subject to definite bounds, but it will usually be an effective therapeutic amount, or the equivalent on a molar basis of the pharmacologically-active form produced upon the metabolic release of the active drug (2-acetoxybenzoic acid) to achieve its desired pharmacological or physiological effect.

Although the present invention has been adequately described in the foregoing specification, it is apparent that various changes and/or modifications can be made thereto by the skilled artisan without departing from the spirit and scope thereof. Such changes and/or modifications are properly, equitably and intended to be within the full range of equivalence of the following claims:

What is claimed is:

1. An 1-O-(2'acetoxy)benzyl-α-D-2-deoxyglucopyranose derivative having the formula

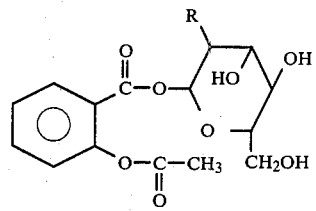

wherein R represents amino, lower monoalkylamino, lower dialkylamino, piperidino, lower alkyl, lower cycloalkyl, lower alkoxy or hydroxy-substituted lower alkyl.

2. A method for inducing an analgesic, antipyretic, antirheumatic or anti-inflammatory response in a warm-blooded animal which comprises orally administering thereto an effective amount of 1-O-(2'-acetoxy)benzoyl-α-D-2-deoxyglucopyranose derivative as defined in claim 1.

3. A pharmaceutical composition of matter adapted for oral administration comprising an effective analgesic, antipyretic, antirheumatic or anti-inflammatory amount of an 1-O-(2'-acetoxy)benzoyl-α-D-2-deoxyglucopyranose derivative as defined in claim 1 and a pharmaceutically acceptable inert carrier.

4. The compound as defined by claim 1, wherein R is amino.

5. The compound as defined in claim 1, wherein R is lower alkyl.

6. The compound as defined in claim 1, wherein R is lower monoalkylamino.

7. The compound as defined in claim 1, wherein R is lower dialkylamino.

8. The compound as defined in claim 1, wherein R is piperidino.

9. The compound as defined in claim 1, wherein R is lower cycloalkyl.

10. The compound as defined in claim 1, wherein R is lower alkoxy.

11. The compound as defined in claim 1, wherein R is hydroxy-lower alkyl.

12. The compound as defined by claim 5, wherein R is methyl.

13. The compound as defined by claim 11, wherein R is 2-hydroxyalkyl.

14. A compound having the structural formula:

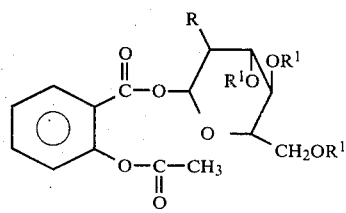

wherein R represents amino, lower monoalkylamino, lower dialkylamino, piperidino, lower alkyl, lower cycloalkyl, lower alkoxy or hydroxy-substituted lower alkyl, and $R^1$ is selected from the group consisting of benzyl, p-methoxybenzyl and tert-butyl.

15. The method as defined by claim 2, for inducing an analgesic response.

16. The method as defined by claim 2, for inducing an antipyretic response.

17. The method as defined by claim 2, for inducing an antirheumatic response.

18. The method as defined by claim 2, for inducing an anti-inflammatory response.

19. The composition as defined by claim 3, comprising an analgesic amount of said derivative.

20. The composition as defined by claim 3, comprising an antipyretic amount of said derivative.

21. The composition as defined by claim 3, comprising an antirheumatic amount of said derivative.

22. The composition as defined by claim 3, comprising an anti-inflammatory amount of said derivative.

* * * * *